(12) United States Patent
Nishizaka et al.

(10) Patent No.: US 7,517,534 B2
(45) Date of Patent: *Apr. 14, 2009

(54) OIL-IN-WATER EMULSIONS AND PROCESS FOR PRODUCING THE SAME

(75) Inventors: Takahiro Nishizaka, Wakayama (JP); Takeshi Ihara, Wakayama (JP); Tomohito Kitsuki, Wakayama (JP)

(73) Assignee: Kao Corporation, Tokyo (JP)

( * ) Notice: Subject to any disclaimer, the term of this patent is extended or adjusted under 35 U.S.C. 154(b) by 535 days.

This patent is subject to a terminal disclaimer.

(21) Appl. No.: 10/471,699

(22) PCT Filed: Mar. 12, 2002

(86) PCT No.: PCT/JP02/02291

§ 371 (c)(1),
(2), (4) Date: Sep. 15, 2003

(87) PCT Pub. No.: WO02/074261

PCT Pub. Date: Sep. 26, 2002

(65) Prior Publication Data

US 2004/0166078 A1     Aug. 26, 2004

(30) Foreign Application Priority Data

Mar. 16, 2001 (JP) .............................. 2001-76600
Nov. 27, 2001 (JP) .............................. 2001-361255

(51) Int. Cl.
  *A61K 8/02* (2006.01)
(52) U.S. Cl. ..................................... 424/401; 514/938
(58) Field of Classification Search .................. 424/401; 514/938
See application file for complete search history.

(56) References Cited

U.S. PATENT DOCUMENTS

| 4,096,074 A | 6/1978 | Stournas |
| 4,663,448 A | 5/1987 | Chiu |
| 5,912,294 A | 6/1999 | Schade |

FOREIGN PATENT DOCUMENTS

| EP | 1191039 A1 | 3/2002 |
| JP | 59-98727 A | 6/1984 |
| JP | 3-291295 A | 12/1991 |
| JP | 10-338714 A | 12/1998 |
| WO | WO-97/31950 A1 | 9/1997 |
| WO | WO 00/73351 A1 | 12/2000 |

*Primary Examiner*—Sreeni Padmanabhan
*Assistant Examiner*—Renee Claytor
(74) *Attorney, Agent, or Firm*—Birch, Stewart, Kolasch & Birch, LLP

(57) ABSTRACT

A process for the preparation of an o/w emulsion, which comprises mixing together a high molecular compound carrying at least on side chains thereof groups represented by the following formula (1):

$$—(OX)_n-E^2-R \quad (1)$$

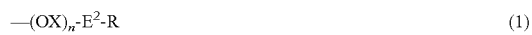

wherein n "X"s may be the same or different and each independently represents a linear or branched, divalent, saturated $C_{1-6}$ hydrocarbon group, n stands for a number of from 5 to 300, $E^2$ represents an ether bond or an oxycarbonyl group (—OCO— or —COO—), and R represents a linear or branched, $C_{4-30}$ alkyl group which may be substituted by hydroxyl group(s), an aqueous solution of a water-soluble polyol, and a hydrophobic compound, and diluting a resulting mixture with water, and the o/w emulsion obtained by the preparation process.

The emulsion according to the present invention is excellent in touch feeling to the skin and is good in stability.

5 Claims, No Drawings

OIL-IN-WATER EMULSIONS AND PROCESS FOR PRODUCING THE SAME

This application is the national phase under 35 U.S.C. § 371 of PCT International Application No. PCT/JP02/02291 which has an International filing date of Mar. 12, 2002, which designated the United States of America.

TECHNICAL FIELD

This invention relates to o/w emulsions excellent in resistance to surfactant solutions and a preparation process thereof.

BACKGROUND ART

It is an important technique for products such as cosmetics and perfumes to stably incorporate hydrophobic substances such as oils as emulsions. In general, an emulsion making use of a low molecular surfactant is relatively stable as emulsified particles are small, but the emulsified particles are so small that oiliness is felt when applied to the skin. An emulsion making use of a high molecular compound, on-the other hand, provides relatively large particles and is excellent to the feel of the skin when applied, but it is accompanied by a drawback that the emulsion is less stable. JP-A-59-0098727 discloses a process for preparing a stable emulsion by mixing an oil component with a glycopeptide and a polyhydric alcohol and diluting the resultant mixture with water to reduce the particle size. As the resulting emulsified particles are small in size, there remains the drawback of the inherent oily feeling of the emulsion upon application.

On the other hand, in a solution system containing a large amount of surfactant, such as in a detergent, even an emulsion having a small emulsified particle size which is considered to be stable may lose its stability, and the emulsified state is thus broken. Even when a hydrophobic substance useful for washing surfaces of the skin or hair is added as an emulsion, the hydrophobic substance is emulsified by a surfactant employed as a detergent so that the forming property of the detergent deteriorates. Further, the hydrophobic substance, despite its additional incorporation, is emulsified by the surfactant used as the detergent in such a case. Most of the hydrophobic substance so added is, therefore, washed off, leading to a problem that it is very difficult to make the hydrophobic substance remain on the washed surface after use.

An object of the present invention is, therefore, to provide an o/w emulsion which is stable even in a system having a large amount of a surfactant, as in a detergent, that is, excellent in resistance to surfactant solutions which can be added to detergents without impairing its basic performance such as foaming and excellent to the feel of the skin when applied, and also a preparation process of the same.

DISCLOSURE OF THE INVENTION

The present applicant has already developed novel polysaccharide derivatives having excellent water-solubility, unique behavior of increasing viscosity and stabilizing effect for hydrophobic substances, and filed thereon an application for a patent (WO 00/73351).

An object of the present invention is to provide an o/w emulsion in which oil droplets are stably dispersed and the stable form of the emulsion is retained even in the presence of a surfactant at a high concentration, and also a preparation process of the same.

The present inventors have found that by using a high molecular compound containing groups represented by the below-described formula (1) on a part of the side chains thereof, preparing a specific composition containing the high molecular compound and a hydrophobic compound, and by diluting the composition with water, there can be provided an emulsion of the hydrophobic compound having good stability, leading to the present invention.

Specifically, the present invention provides an o/w emulsion obtained by mixing together a high molecular compound carrying at least on side chains thereof groups represented by the following formula (1):

$$—(OX)_n\text{-}E^2\text{-}R \qquad (1)$$

wherein n "X"s may be the same or different and each independently represents a linear or branched, divalent, saturated $C_{1-6}$ hydrocarbon group, n stands for a number of from 5 to 300, $E^2$ represents an ether bond or an oxycarbonyl group (—OCO— or —COO—), and R represents a linear or branched, $C_{4-30}$ alkyl group which may be substituted by one or more hydroxyl groups, an aqueous solution of a water-soluble polyol, and a hydrophobic compound, and diluting the resulting mixture with water, and a preparation process of the same.

BEST MODES FOR CARRYING OUT THE INVENTION

As the high molecular compound which carries on a part of the side chains thereof groups represented by formula (1) and is employed in the present invention, preferred is a high molecular compound wherein the molecular weight may be preferably from 10,000 to 10,000,000, more preferably from 10,000 to 2,000,000, even more preferably from 30,000 to 1,500,000. In formula (1), X is preferably from 2 to 4, n is preferably a number from 8 to 120, and R preferably has a carbon number from 6 to 25.

Specific examples of the high molecular compound include hydrophobized polysaccharides carrying groups represented by formula (1), and synthetic water-soluble high molecular compounds which have a molecular weight of from 10,000 to 2,000,000, preferably from 30,000 to 1,500,000 and carry groups of formula (1) added at a rate of from 0.0001 to 0.1 group, preferably from 0.001 to 0.05 group per backbone monomer.

Examples of the hydrophobized polysaccharides can include substituted polysaccharides in which a part or all of the hydrogen atoms of the hydroxyl groups in the polysaccharide or a derivative thereof are substituted by the following groups (A):

(A) groups represented by the following formula (2):

$$\text{-}E^1\text{-}(OX)_n\text{-}E^2\text{-}R \qquad (2)$$

wherein $E^1$ represents a linear or branched, divalent, saturated $C_{1-6}$ hydrocarbon group which may be substituted by hydroxyl group(s) or oxo group(s), n stands for a number of from 8 to 300, n "X"s may be the same or different and each independently represents a linear or branched, divalent, saturated $C_{1-6}$ hydrocarbon group, $E^2$ represents an ether bond or an oxycarbonyl group (—OCO— or —COO—), and R represents a linear or branched, $C_{4-30}$ alkyl group which may be substituted by hydroxyl group(s), and are optionally substituted by one or more groups selected from the following groups (B), (C) and (D):

(B) $C_{1-5}$ sulfoalkyl groups or salts thereof, each of which may be substituted by hydroxyl group(s), (C) $C_{2-6}$ carboxyalkyl groups or salts thereof, each of which may be substituted by hydroxyl group(s), and (D) groups represented by the following formula (3):

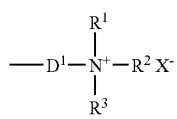
(3)

wherein $D^1$ represents a linear or branched, divalent, saturated $C_{1-6}$ hydrocarbon group which may be substituted by hydroxyl group(s), $R^1$, $R^2$ and $R^3$ may be the same or different and each independently represents a linear or branched, $C_{1-3}$ alkyl group which may be substituted by hydroxyl group(s), and $X^-$ represents a hydroxide ion, halide ion or organic acid ion, in which the hydrogen atom(s) of the hydroxyl group(s) in each of the groups (A) to (D) may be substituted further by the groups (A), (B), (C) or (D).

Examples of the polysaccharide or its derivative usable in the present invention include polysaccharides such as cellulose, guar gum, starch, pullulan, dextran, fructan, mannan, agar, carrageenan, chitin, chitosan, pectin, alginic acid, and hyaluronic acid; and their derivatives having substituent groups such as methyl groups, ethyl groups, hydroxyethyl groups, hydroxypropyl groups or the like. These substituent groups can be introduced either alone or in combination into constituent monosaccharide residual groups. Illustrations of the polysaccharide derivative are hydroxyethylcellulose, hydroxyethyl ethylcellulose, hydroxyethylguar gum, hydroxyethyl starch, methylcellulose, methylguar gum, methylstarch, ethylcellulose, ethylguar gum, ethylstarch, hydroxypropylcellulose, hydroxypropylguar gum, hydroxypropyl starch, hydroxyethylmethylcellulose, hydroxyethylmethylguar gum, hydroxyethyl methyl starch, hydroxypropyl methylcellulose, hydroxypropyl methylguar gum, and hydroxypropyl methylstarch. Among these polysaccharides and derivatives thereof, cellulose, starch, hydroxyethylcellulose, methylcellulose, ethylcellulose and hydroxypropylcellulose are preferred, with hydroxyethylcellulose being particularly preferred. The weight average molecular weights of these polysaccharides or their derivatives is preferably in a range of from 10,000 to 10,000,000, more preferably in a range of from 100,000 to 5,000,000, even more preferably in a range of from 200,000 to 2,000,000.

When a cellulose, for example, is used as the polysaccharide or a derivative thereof, recurring units of the substituted polysaccharide used in the present invention [namely, a polysaccharide or a derivative thereof in which a part or all of the hydrogen atoms of the hydroxy groups are substituted by the above-described groups (A) and optionally substituted by the above-described groups (B), (C) and/or (D)] can be exemplified by the following formula:

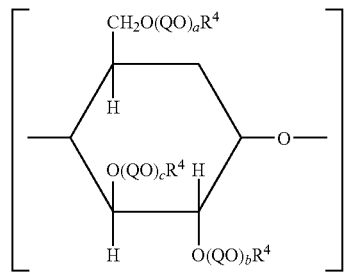

wherein $R^4$ may be the same or different and each independently represents a hydrogen atom or a group selected from a methyl group, an ethyl group, a hydroxyethyl group, a hydroxypropyl group, the polyoxyalkylene-containing substituent group (A) represented by formula (2), the substituent group (B) which is a sulfoalkyl group, the substituent group (C) which is a carboxyalkyl group and the cationic substituent group represented by the formula (3), Q may be the same or different and each independently represents a $C_{2-4}$ alkylene group, a, b and c may be the same or different and each independently represents a number of from 0 to 10, said groups QO, said groups $R^4$, and a, b and c may be the same or different within each recurring unit or between or among recurring units; and hydroxyl group(s) in each of the substituent groups (A) to (D) may be further substituted by the substituent groups (A) to (D), with a proviso that at least the substituent group (A) is contained as $R^4$.

Preferred as $E^1$ in formula (2) for the polyoxyalkylene-containing substituent (A) are linear or branched, divalent, saturated $C_{2-3}$ hydrocarbon groups each of which may be substituted by hydroxyl group(s) or oxo group(s). Specifically, ethylene, propylene, trimethylene, 2-hydroxytrimethylene, 1-hydroxymethyl-ethylene, 1-oxoethylene, 1-oxotrimethylene, 1-methyl-2-oxoethylene and the like are preferred.

As X in formula (2), linear or branched, divalent, saturated $C_{2-3}$ hydrocarbon groups are preferred. Specifically, ethylene, propylene and trimethylene are preferred. The polymerization degree of (—OX—) as indicated by n is preferably 8 to 120, especially 10 to 60 from the standpoint of its thickening effect and emulsion stability. n "X"s may be the same or different. The letter "n" as used herein means an average number of moles of added OXs. Although $E^2$ represents an ether bond or an oxycarbonyl group, an ether bond is preferred.

Preferred as R in formula (2) are linear or branched alkyl groups each of which has 5 to 25 carbon atoms, especially 6 to 20 carbon atoms and may be substituted by hydroxyl group(s). From the standpoint of stability, on the other hand, unsubstituted alkyl groups, especially unsubstituted linear alkyl groups are preferred. Specifically, octyl, decyl, dodecyl, tetradecyl, hexadecyl, octadecyl, isostearyl and the like are preferred.

The degree of substitution by the substituent groups (A) in the substituted polysaccharide according to the present invention is preferably in a range of from 0.0001 to 1.0, more preferably in a range of from 0.0005 to 0.5, even more preferably in a range of from 0.001 to 0.1 per constituent monosaccharide residual group.

In addition to the substituent groups (A), the substituted polysaccharide according to the present invention may be substituted further by one or more groups selected from the above-described substituent groups (B), (C) and (D). In addition, the hydrogen atom(s) of the hydroxyl group(s) in each of the substituent groups (A) to (D) may be substituted further by the substituent groups (A) to (D).

Illustrations of the substituent groups (B), that is, $C_{1-5}$ sulfoalkyl groups or salts thereof, each of which may be substituted by hydroxyl group(s) are 2-sulfoethyl, 3-sulfopropyl, 3-sulfo-2-hydroxypropyl, and 2-sulfo-1-(hydroxymethyl)ethyl. Among these, 3-sulfo-2-hydroxypropyl is preferred from the viewpoint of stability and production. All or a part of these substituent groups (B) may be in the form of salts with Group 1 or Group 2 elements such as Na, K, Ca or Mg or organic cations such as an amine or ammonium. The degree of substitution by these substituents (B) may be preferably in a range of from 0 to 1.0, more preferably in a range of from 0 to 0.8, even more preferably in a range of from 0 to 0.5 per constituent monosaccharide residual group.

Illustrations of the substituent groups (C), that is, $C_{2-6}$ carboxyalkyl groups or salts thereof, each of which may be substituted by hydroxyl group(s) are carboxymethyl, carboxyethyl, carboxypropyl, carboxybutyl, and carboxypentyl. Among these, carboxymethyl is preferred from the viewpoint of stability and production. All or a part of these substituent groups (C) may be in the form of salts with Group 1 or Group 2 elements such as Na, K, Ca or Mg or organic cations such as an amine or ammonium. The degree of substitution by these substituents (C) is preferably in a range of from 0 to 1.0, more preferably in a range of from 0 to 0.8, even more preferably in a range of from 0 to 0.5 per constituent monosaccharide residual group.

As $D^1$ in each cationic substituent group (D) represented by the following formula (3):

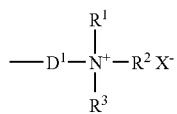

(3)

wherein $D^1$, $R^1$, $R^2$, $R^3$ and $X^-$ are as defined above, linear or branched, divalent, saturated $C_{2-3}$ hydrocarbon groups each of which may be substituted by hydroxyl group(s) are preferred. Specifically, ethylene, propylene, trimethylene, 2-hydroxytrimethylene, 1-hydroxymethylethylene and the like are preferred.

Examples of $R^1$, $R^2$ and $R^3$ in each cationic substituent group (D) can include methyl, ethyl, propyl and 2-hydroxyethyl, with methyl and ethyl being preferred.

Examples of the halogen ion represented by $X^-$ in each cationic substituent group (D) can include a chloride ion, a bromide ion and an iodide ion. Examples of the organic acid ion can include $CH_3COO^-$, $CH_3CH_2COO^-$ and $CH_3(CH_2)_2COO^-$. Preferred examples of $X^-$ include a hydroxide ion, a chloride ion and a bromide ion.

The degree of substitution by these cationic substituent groups (D) is preferably in a range of from 0 to 0.5, even more preferably in a range of from 0 to 0.3 per constituent monosaccharide residual group.

The substitution of the polysaccharide or the derivative thereof with one or more of the substituent groups (A) to (D), namely, polyoxyalkylenization, sulfoalkylation, carboxyalkylation or cationization, can be carried out by the process disclosed in WO 00/73351.

The synthetic, water-soluble, high molecular compound, which has a molecular weight of from 10,000 to 2,000,000 and is represented by formula (1) in which X is an ethylene oxide (EO) group, n is a number of from 5 to 200 and R is a linear or branched $C_{4-30}$ alkyl group, that is, $C_{4-30}$ hydrophobic groups each provided with 5 to 200 EO linkages are added to a backbone monomer at a rate of from 0.0001 to 0.1 group per backbone monomer, can be obtained by reacting a water-soluble, synthetic, high molecular compound having hydroxyl groups such as polyvinyl alcohol or polyglycidol with a compound represented by the following formula (4):

$$E^3\text{-}(OX)_n\text{-}E^2\text{-}R \quad (4)$$

wherein $E^3$ represents a $C_{3-6}$ epoxylated alkyl group, a linear or branched, halogenated $C_{1-6}$ alkyl group which may be substituted by hydroxyl group(s), or a carboxyl group or $C_{2-6}$ carboxyalkyl group or a derivative thereof, and X, n and R have the same meanings as defined above. As an alternative, it can also be obtained by copolymerizing a water-soluble monomer and a monomer having a $C_{4-30}$ hydrophobic group bonded via 5 to 200 EO linkages.

The water-soluble monomer can be of the following formula (5):

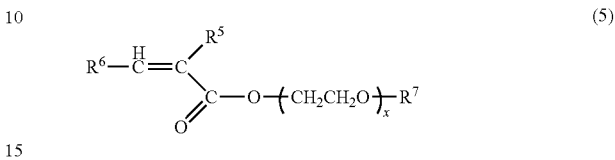

(5)

wherein $R^5$, $R^6$ and $R^7$ may be the same or different and each independently represents a hydrogen atom or a methyl group, and X stands for a number of from 2 to 100, or the following formula (6):

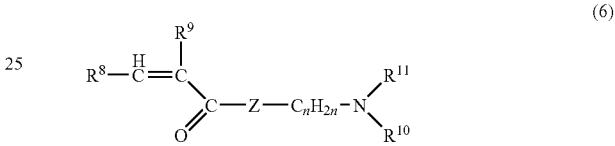

(6)

wherein $R^8$ and $R^9$ may be the same or different and each independently represents a hydrogen atom or a methyl group, $R^{10}$ and $R^{11}$ each independently represents a methyl group or an ethyl group, n stands for an integer of 0 or 2 to 5, and Z represents an NH group, an oxygen atom, or connecting bond. Although these monomers can be synthesized by known processes, commercial products may be used as available. As such commercial products, examples include "BLEMMER PME-100", "BLEMMER PME-200", "BLEMMER PME-400", "BLEMMER PME-1000" and "BLEMMER PME-4000" (products of NOF CORPORATION, methoxypolyethylene glycol monomethacrylate), "BLEMMER AME-400" (product of NOF CORPORATION, methoxypolyethylene glycol monoacrylate), "BLEMMER PE-90", "BLEMMER PE-200" and "BLEMMER PE-350" (all, products of NOF CORPORATION, polyethylene glycol monomethacrylate), "BLEMMER AE-90", "BLEMMER AE-200" and "BLEMMER AE-400" (all, products of NOF CORPORATION, polyethylene glycol monoacrylate), DMAEA (N,N-dimethylaminoethyl acrylate), DMAPAA (N,N-dimethylaminopropylacrylamide), DMAA (N,N-dimethylacrylamide) and DEAA (N,N-diethylacrylamide) (all, products of Kohjin Co., Ltd.), etc.

Examples of the monomer having the $C_{4-30}$ hydrophobic group bonded via 5 to 200 EO linkages can include compounds of the following formula (7):

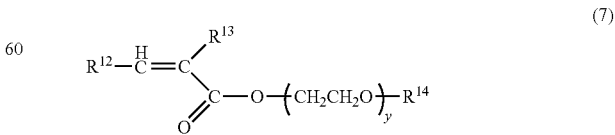

(7)

wherein $R^{12}$ and $R^{13}$ may be the same or different and each independently represents a hydrogen atom or a methyl group, y stands for a number of from 5 to 200, and $R^{14}$ represents a linear or branched $C_{8-30}$ alkyl group which may be substituted by hydroxyl group(s). Although they can be synthesized by known processes, commercial products may be used as available. As such commercial products, examples include "BLEMMER ALE-800" (lauroxypolyethylene glycol monoacrylate), "BLEMMER PSE-400" and "BLEMMER PSE-1300" (stearoxypolyethylene glycol monomethacrylate) (all, products of NOF CORPORATION).

The water-soluble polyol for use in the present invention is a polyhydric alcohol having two or more hydroxyl groups in its molecule. Specific examples can include alkylene glycol such as ethylene glycol, propylene glycol, 1,3-butylene glycol and 1,4-butylene glycol, polyalkylene glycols such as dipropylene glycol, sugar alcohols such as glucose, maltose, maltitose, sucrose, fructose, xylitol, sorbitol, maltotriose and threitol, glycerol, polyglycerol, erythritol, and starch alcohols. These water-soluble polyols can be used either alone or in combination.

Illustrations of the hydrophobic compound are higher alcohols, sterols, silicones, fluorine-containing oils, oil components and the like, which are added to heighten the functions and additional values of toiletry products.

Examples of the higher alcohols include benzyl alcohol, isocetyl alcohol, isostearyl alcohol, behenyl alcohol, hexadecyl alcohol, phenylethyl alcohol, cetanol, stearyl alcohol, oleyl alcohol, 2-octyldodecanol, batyl alcohol, and 2-hexyldecanol, with cetanol and stearyl alcohol being particularly preferred.

Examples of the stenols can include cholesterol, cholesteryl isostearate, provitamin $D_3$, campesterol, stigmastanol, stigmastenol, 5-dihydrocholesterol, α-spinasterol, palesterol, clionasterol, γ-citosterol, stigmastenol, sargasterol, apenasterol, ergostanol, citosterol, colbisterol, chondrillasterol, polyferrasterol, haliclonasterol, neospongosterol, fucosterol, aptostanol, ergostadienol, ergosterol, 22-dihydroergosterol, brassicasterol, 24-methylenecholesterol, 5-dihydroergosterol, dehydroergosterol, fungisterol, cholestanol, coprostanol, zymosterol, 7-ketocholesterol, latosterol, 22-dehydrocholesterol, β-citosterol, cholestatrien-3β-ol, coprostanol, cholestanol, ergosterol, 7-dehydrocholesterol, 24-dehydrocholestadion-3β-ol, equilenin, equilin, estron, 17β-estradiol, androst-4-ene-3β,17β-diol, dehydroepiandrosterone, and cholesteryl alkenylsuccinates (JP-A-050294989). Among these, cholesterol, cholesteryl isostearate and cholesteryl alkenylsuccinates are particularly preferred.

The silicones are those commonly added in toiletry products. For example, in addition to octamethylpolysiloxane, tetradecamethylpolysiloxane, methylpolysiloxane, highly-polymerized methylpolysiloxane and methylphenylpolysiloxane, they also include methylpolysiloxanes such as octamethylcyclotetrasiloxane and decamethylcyclopentanesiloxane, trimethylsiloxysilicate, and modified silicones such as alkyl-modified silicones, polyether- and alkyl-modified silicones, amino-modified silicone, fluorine-modified silicone, alkyl-glyceryl-ether-modified silicones, and modified organopolysiloxanes disclosed in JP-A-060072851.

Preferred examples of the fluorine-containing oils include perfluoropolyethers, i.e. perfluoroorganic compounds which are liquid at room temperature, and fluorine-modified silicones, for example, perfluorodecalin, perfluoroadamantane, perfluorobutyltetrahydrofuran, perfluorooctane, perfluorononane, perfluoropentane, perfluorodecane, perfluorododecane, and perfluoropolyethers.

Further, the oil components may be either volatile or non-volatile. Examples of the oil components are hydrocarbons such as solid or liquid paraffin, vaseline, crystal oil, ceresin, ozokerite, montan wax, squalane, and squalene; Eucalyptus oil, mentha oil, camellia oil, macadamia nut oil, avocado oil, beef tallow, lard, horse grease, yolk oil, olive oil, carnauba wax, lanolin, and jojoba oil; ester oils such as glyceryl monostearate, glyceryl distearate, glyceryl monooleate, isopropyl palmitate, isopropyl stearate, butyl stearate, isopropyl myristate, neopentyl glycol dicaprylate, diethyl phthalate, myristyl lactate, diisopropyl adipate, cetyl myristate, myristyl lactate, diisopropyl adipate, cetyl myristate, cetyl lactate, 1-isostearoyl-3-myristoylglycerol, cetyl 2-ethylhexanoate, 2-ethylhexyl palmitate, 2-octyldecyl myristate, neopentyl glycol di(2-ethylhexanoate), 2-octyldodecyl oleate, glyceryl triisostearate, and glyceryl di(p-methoxycinnamate)-mono(2-ethylhexanoate); higher fatty acids such as stearic acid, palmitic acid, and oleic acid; natural essential oils such as rosemary, rooibos, royal jelly, and witch-hazel leave oil; and function oil substances such as lignan, vitamin E, oil-soluble vitamin C, vitamin A derivatives, ceramides, substances structurally analogous to ceramides, oil-soluble ultraviolet absorbers, and fragrances.

According to the process of the present invention, an emulsion of a hydrophobic compound may be prepared by diluting with water a composition (1) composed in admixture of 1 part by weight of a substituted polysaccharide, 2 to 50 parts by weight of one or more of water-soluble polyols, 5 to 30 parts by weight of water and 0.01 to 70 parts by weight of the hydrophobic compound.

In a preferred embodiment of the present invention, the substituted polysaccharide, the water-soluble polyol and the water (or the substituted polysaccharide and an aqueous solution of the water-soluble polyol) are at first mixed to obtain a composition (1a), and then the hydrophobic compound is mixed further to produce the composition (1). In this process, the content of the substituted polysaccharide, the content of the water-soluble polyol and the content of the water in the composition (1a) may preferably range from 1 to 10 wt. %, from 10 to 90 wt. % and from 10 to 90 wt. %, respectively. Further, the weight ratio of the water-soluble polyol to water may preferably range from 10/90 to 90/10. Here, it is more preferred to produce the composition (1a) by mixing the water-soluble polyol and the water beforehand to prepare an aqueous solution of the water-soluble polyol and then mixing the aqueous solution and the substituted polysaccharide together preferably under stirring.

The amount of the hydrophobic compound to be mixed with the composition (1a) may range preferably from 0.01 to 70 parts by weight, more preferably from 0.1 to 50.0 parts by weight, even more preferably from 1.0 to 45.0 parts by weight per part by weight of the substituted polysaccharide contained in the composition (1a).

No particular limitation is imposed on the manner of mixing, but under appropriate mixing mechanical force, the hydrophobic compound may be added to the composition (1a) at once or gradually and continuously or by dividing a predetermined amount into portions. It is preferred to appropriately adjust the flow rate of the dropwise addition or the number of adding the divided hydrophobic compound to obtain a well-mixed state, although no Particular limitation is imposed thereon. The predetermined amount of the hydrophobic compound is mixed in its entirety so that the composition (1) is obtained.

In another embodiment of the present invention, the composition (1) can also be obtained as will be described next. Specifically, the substituted polysaccharide and the hydrophobic compound are mixed to prepare a composition (1b). The amount of the hydrophobic compound in the composition (1b) may range preferably from 0.01 to 70 parts by weight, more preferably from 0.1 to 50 parts by weight, particularly preferably from 1.0 to 45 parts by weight per part by weight of the substituted polysaccharide contained in the composition (1b).

The composition (1b) and an aqueous solution of the water-soluble polyol are next mixed together under. stirring to produce the above-described composition (1). In this production, the content of the water-soluble polyol in the composition (1) may range preferably from 2 to 50 parts by weight, more preferably from 2 to 40 parts by weight, even more preferably from 4 to 35 parts by weight per part by weight of the substituted polysaccharide.

No particular limitation is imposed on the manner of mixing, but under appropriate mixing mechanical force, the aqueous solution of the polyol may be added to the composition (1b) at once or gradually and continuously or by dividing a predetermined amount into portions. It is preferred to appropriately adjust the flow rate of the dropwise addition or the number of adding the divided polyol to obtain a well-mixed state, although no particular limitation is imposed thereon. The predetermined amount of the hydrophobic compound is mixed in its entirety so that the composition (1) is obtained.

The composition (1) is next mixed with water to obtain an aimed emulsion. No particular limitation is imposed on the manner of mixing with water, and the mixing is conducted under adequate mechanical force which varies depending upon the viscosity of the composition (2) and the amount of water to be mixed. The amount of water to be mixed may be such an amount that the weight ratio of the composition (1) to water ranges preferably from 1/99 to 99/1, more preferably from 1/99 to 65/35, even more preferably from 1/99 to 50/50.

The average particle size of emulsified particles of the hydrophobic compound, which exist in the emulsion, can be measured, for example, by a "Model TA-II Coulter Counter" in accordance with a method to be described below. The average particle size may range from 2 to 30 μm, with 3 to 20 μm being more preferred.

The emulsions so obtained can be used as cosmetics, massaging cosmetic preparations, skin care preparations and the like. To provide these products with additional values, however, various additives commonly employed in these products may also be incorporated such as surfactants, dispersants, solvents, fragrances, dyes, inorganic salts, preservatives, antioxidants and pH adjusters. In particular, the emulsions obtained by the present invention show good stability without bringing about time-dependent external changes such as viscosity changes or separation even when surfactants are contained.

EXAMPLES

In the following Examples, the degrees of substitution by substituent groups (A) in substituted polysaccharides (hereinafter called polysaccharide derivatives) according to the present invention were determined by the Zeisel method [D. G. Anderson, Anal. Chem., 43, 894 (1971)], while the degrees of substitution by sulfoalkyl groups (B), carboxyalkyl groups (C) and cationic substituent groups (D), respectively, in the polysaccharide derivatives were determined by the colloidal titration method. Incidentally, the term "degree of substitution" to be used in the following examples indicates the average number of substituent groups per constituent monosaccharide residual group.

Preparation Example 1

Preparation of Polysaccharide Derivative 1

Hydroxyethylcellulose having a weight average molecular weight of about 800,000 and a degree of substitution by hydroxyethyl groups of 1.8 (80 g; "HEC-QP15000H", product of Union Carbide Corp.), isopropyl alcohol (640 g) and p-toluenesulfonic acid (2.0 g) were mixed to prepare a slurry, followed by stirring at room temperature for 30 minutes under a nitrogen gas atmosphere. To the solution, a compound (15 g) represented by the following formula:

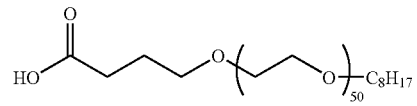

was added, and a reaction was conducted at 80° C. for 8 hours to effect polyoxyalkylenization. After completion of the reaction, the reaction mixture was neutralized with a 48% aqueous solution of sodium hydroxide, and the reaction product was collected by filtration. The reaction product was washed twice with 80% isopropyl alcohol (500 g) and twice with isopropyl alcohol (500 g), and dried one day and night at 70° C. under reduced pressure to obtain a hydroxyethylcellulose derivative (Polysaccharide Derivative 1)(73.4 g).

The degree of substitution of the resultant hydroxyethylcellulose derivative by polyoxyalkylene-containing substituent groups (A) was 0.010.

Preparation Example 2

Preparation of Polysaccharide Derivative 2

Potato starch (80 g; product of Katayama Chemical Industries Co., Ltd.), 50% isopropyl alcohol (640 g) and a 48% aqueous solution of sodium hydroxide (5.5 g) were mixed to prepare a slurry, followed by stirring at room temperature for 30 minutes under a nitrogen gas atmosphere. To the solution, a compound (19.0 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with 50% isopropyl alcohol (500 g) and then twice with acetone (500 g), and dried one day and night at 70° C. under reduced pressure to obtain a polyoxyalkylenized starch derivative (Polysaccharide Derivative 2) (69.4 g).

The degree of substitution of the resultant starch derivative by polyoxyalkylene-containing substituent groups (A) was 0.005.

Preparation Example 3

Preparation of Polysaccharide Derivative 3

To the polyoxyalkylenized starch derivative (20.0 g) obtained in Preparation Example 2, 70% isopropyl alcohol (200 g), sodium 3-chloro-2-hydroxypropanesulfonate (42.6 g) and a 48% aqueous solution of sodium hydroxide (18.0 g) were added, followed by sulfonation at 50° C. for 5 hours. After completion of the reaction, the reaction mixture was neutralized with acetic acid, and the reaction product was collected by filtration. The reaction product was washed thrice with 70% isopropyl alcohol (400 g) and twice with isopropyl alcohol (300 g), and dried one day and night at 70° C. under reduced pressure to obtain a polyoxyalkylenized and sulfonated starch derivative (Polysaccharide Derivative 3) (38.3 g).

The degree of substitution of the resultant starch derivative by 3-sulfo-2-hydroxypropyl groups (substituent groups (B)) was 0.301.

Preparation Example 4

Preparation of Polysaccharide Derivative 4

The polyoxyalkylenized starch (35.5 g) obtained in Preparation Example 2, 70% isopropyl alcohol (350 g) and a 48% aqueous solution of sodium hydroxide (2.4 g) were mixed to prepare a slurry, followed by stirring at room temperature for 30 minutes under a nitrogen gas atmosphere. To the reaction mixture, sodium monochloroacetate (25.1 g) and a 48% aqueous solution of sodium hydroxide (18.0 g) were added, and carboxymethylation was conducted at 50° C. for 5 hours. After completion of the reaction, the reaction mixture was neutralized with acetic acid, and the reaction product was collected by filtration. The reaction product was washed thrice with 70% isopropyl alcohol (400 g) and twice with isopropyl alcohol (300 g), and dried one day and night at 70° C. under reduced pressure to obtain a polyoxyalkylenized and carboxymethylated starch derivative (Polysaccharide Derivative 4) (33.8 g). The degree of carboxymethylation (the degree of substitution by substituent groups (C)) of the resultant starch derivative was 0.48.

Preparation Example 5

Preparation of Polysaccharide Derivative 5

The polyoxyalkylenized starch (35.5 g) obtained in Preparation Example 2, 70% isopropyl alcohol (350 g) and a 48% aqueous solution of sodium hydroxide (2.4 g) were mixed to prepare a slurry, followed by stirring at room temperature for 30 minutes under a nitrogen gas atmosphere. To the reaction mixture, a 60% aqueous solution of (3-chloro-2-hydroxypropyl)trimethyl ammonium chloride (7.0 g) and a 48% aqueous solution of sodium hydroxide (2.0 g) were added, and cationization was conducted at 50° C. for 1 hour. After completion of the reaction, the reaction mixture was neutralized with acetic acid, and the reaction product was collected by filtration. The reaction product was washed thrice with 70% isopropyl alcohol (400 g) and twice with isopropyl alcohol (300 g), and dried for 24 hours at 70° C. under reduced pressure to obtain a polyoxyalkylenized and cationized starch derivative (Polysaccharide Derivative 5) (34.2 g). The degree of cationization (the degree of substitution by substituent groups (D)) of the resultant starch derivative was 0.10.

Preparation Example 6

Preparation of Polysaccharide Derivative 6

Hydroxyethylcellulose having a weight average molecular weight of 1,500,000 and a degree of substitution by hydroxyethyl groups of 1.8 (80 g; "HEC-QP100MH", product of Union Carbide Corp.), 80% isopropyl alcohol (640 g) and a 48% aqueous solution of sodium hydroxide (5.34 g) were mixed to prepare a slurry, followed by stirring at room temperature for 30 minutes under a nitrogen gas atmosphere. To the solution, a compound (12.78 g) represented by the following formula:

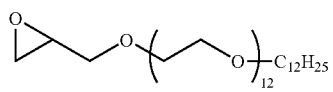

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (500 g), and dried for one day and night at 60° C. under reduced pressure to obtain a polyoxyalkylenized hydroxyethylcellulose derivative (Polysaccharide Derivative 6) (72.0 g).

The degree of substitution of the resultant hydroxyethylcellulose derivative by polyoxyalkylene-containing substituent groups (A) was 0.004.

Preparation Example 7

Preparation of Polysaccharide Derivative 7

Hydroxyethylcellulose having a weight average molecular weight of 1,500,000 and a degree of substitution by hydroxyethyl groups of 1.8 (80 g; "HEC-QP100MH", product of Union Carbide Corp.), 80% isopropyl alcohol (640 g) and a 48% aqueous solution of sodium hydroxide (5.34 g) were mixed to prepare a slurry, followed by stirring at room temperature for 30 minutes under a nitrogen gas atmosphere. To the solution, a compound (21.7 g) represented by the following formula:

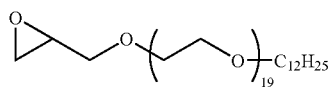

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (500 g), and dried one day and night at 60° C. under reduced pressure to obtain a polyoxyalkylenized hydroxyethylcellulose derivative (Polysaccharide Derivative 7) (74.0 g).

The degree of substitution of the resultant hydroxyethylcellulose derivative by polyoxyalkylene-containing substituent groups (A) was 0.004.

Preparation Example 8

Preparation of Polysaccharide Derivative 8

Hydroxyethylcellulose having a weight average molecular weight of 800,000 and a degree of substitution by hydroxyethyl groups of 1.8 (80 g; "HEC-QP15000H", product of Union Carbide Corp.), 80% isopropyl alcohol (640 g) and a 48% aqueous solution of sodium hydroxide (5.34 g) were mixed to prepare a slurry, followed by stirring at room temperature for 30 minutes under a nitrogen gas atmosphere. To the solution, a compound (13.7 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (500 g), and dried one day and night at 60° C. under reduced pressure to obtain a polyoxyalkylenized hydroxyethylcellulose derivative (Polysaccharide Derivative 8) (69.0 g).

The degree of substitution of the resultant hydroxyethylcellulose derivative by polyoxyalkylene-containing substituent groups (A) was 0.003.

Preparation Example 9

Preparation of Polysaccharide Derivative 9

Hydroxyethylcellulose having a weight average molecular weight of 500,000 and a degree of substitution by hydroxyethyl groups of 1.8 (80 g; "HEC-QP4400H", product of Union Carbide Corp.), water-containing 80% isopropyl alcohol (640 g) and a 48% aqueous solution of sodium hydroxide (5.34 g) were mixed to prepare a slurry, followed by stirring at room temperature for 30 minutes under a nitrogen gas atmosphere. To the solution, a compound (12.78 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (500 g), and dried one day and night at 60° C. under reduced pressure to obtain a polyoxyalkylenized hydroxyethylcellulose derivative (Polysaccharide Derivative 9) (73 g).

The degree of substitution of the resultant hydroxyethylcellulose derivative by polyoxyalkylene-containing substituent groups (A) was 0.004.

Preparation Example 10

Preparation of Polysaccharide Derivative 10

Hydroxyethylcellulose having a weight average molecular weight of 200,000 and a degree of substitution by hydroxyethyl groups of 2.5 (160 g; "NATROZOL250G", product of Hercules Inc.), water-containing 80% isopropyl alcohol (1,280 g) and a 48% aqueous solution of sodium hydroxide (9.8 g) were mixed to prepare a slurry, followed by stirring at room temperature for 30 minutes under a nitrogen gas atmosphere. To the solution, a compound (21.2 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (700 g), and dried one day and night at 60° C. under reduced pressure to obtain a polyoxyalkylenized hydroxyethylcellulose derivative (Polysaccharide Derivative 9) (151 g).

The degree of substitution of the resultant hydroxyethylcellulose derivative by polyoxyalkylene-containing substituent groups (A) was 0.009.

Preparation Example 11

Preparation of Polysaccharide Derivative 11

Hydroxyethylcellulose having a weight average molecular weight of 200,000 and a degree of substitution by hydroxyethyl groups of 2.5 (160 g; "NATROZOL250G", product of Hercules Inc.), water-containing 80% isopropyl alcohol (1,280 g) and a 48% aqueous solution of sodium hydroxide (9.8 g) were mixed to prepare a slurry, followed by stirring at room temperature for 30 minutes under a nitrogen gas atmosphere. To the solution, a compound (31.8 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (700 g), and dried one day and night at 60° C. under reduced pressure to obtain a polyoxyalkylenized hydroxyethylcellulose derivative (Polysaccharide Derivative 9) (152 g).

The degree of substitution of the resultant hydroxyethylcellulose derivative by polyoxyalkylene-containing substituent groups (A) was 0.014.

Preparation Example 12

Preparation of Polysaccharide Derivative 12

Hydroxyethylcellulose having a weight average molecular weight of 200,000 and a degree of substitution by hydroxyethyl groups of 2.5 (160 g; "NATROZOL250G", product of Hercules Inc.), water-containing 80% isopropyl alcohol (1,280 g) and a 48% aqueous solution of sodium hydroxide (9.8 g) were mixed to prepare a slurry, followed by stirring at room temperature for 30 minutes under a nitrogen gas atmosphere. To the solution, a compound (47.7 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (700 g), and dried one day and night at 60° C. under reduced pressure to obtain a polyoxyalkylenized hydroxyethylcellulose derivative (Polysaccharide Derivative 12) (153 g).

The degree of substitution of the resultant hydroxyethylcellulose derivative by polyoxyalkylene-containing substituent groups (A) was 0.021.

Preparation Example 13

Preparation of Polysaccharide Derivative 13

Hydroxyethylcellulose having a weight average molecular weight of 200,000 and a degree of substitution by hydroxyethyl groups of 2.5 (160 g; "NATROZOL250G", product of Hercules Inc.), water-containing 80% isopropyl alcohol (1,280 g) and a 48% aqueous solution of sodium hydroxide (9.8 g) were mixed to prepare a slurry, followed by stirring at room temperature for 30 minutes under a nitrogen gas atmosphere. To the solution, a compound (56.8 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (700 g), and dried one day and night at 60° C. under reduced pressure to obtain a polyoxyalkylenized hydroxyethylcellulose derivative (Polysaccharide Derivative 13) (155 g).

The degree of substitution of the resultant hydroxyethylcellulose derivative by polyoxyalkylene-containing substituent groups (A) was 0.025.

Preparation Example 14

Preparation of Polysaccharide Derivative 14

Hydroxyethylcellulose having a weight average molecular weight of 200,000 and a degree of substitution by hydroxyethyl groups of 2.5 (80 g; "NATROZOL250G", product of Hercules Inc.), water-containing 80% isopropyl alcohol (640 g) and a 48% aqueous solution of sodium hydroxide (4.9 g) were mixed to prepare a slurry, followed by stirring at room temperature for 30 minutes under a nitrogen gas atmosphere.

To the solution, a compound (19.02 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (500 g), and dried one day and night at 60° C. under reduced pressure to obtain a polyoxyalkylenized hydroxyethylcellulose derivative (Polysaccharide Derivative 14) (74 g).

The degree of substitution of the resultant hydroxyethylcellulose derivative by polyoxyalkylene-containing substituent groups (A) was 0.0037.

Preparation Example 15

Preparation of Polysaccharide Derivative 15

Hydroxyethylcellulose having a weight average molecular weight of 200,000 and a degree of substitution by hydroxyethyl groups of 2.5 (60 g; "NATROZOL250G", product of Hercules Inc.), water-containing 80% isopropyl alcohol (480 g) and a 48% aqueous solution of sodium hydroxide (3.67 g) were mixed to prepare a slurry, followed by stirring at room temperature for 30 minutes under a nitrogen gas atmosphere.

To the solution, a compound (39.45 g) represented by the following formula:

was added, and a reaction was conducted at 80° C. for 8 hours to effect polyoxyalkylenization. After completion of the reaction, the reaction mixture was neutralized with acetic acid, and the reaction product was collected by filtration. The reaction product was washed twice with isopropyl alcohol (400 g), and dried one day and night at 60° C. under reduced pressure to obtain a polyoxyalkylenized hydroxyethylcellulose derivative (Polysaccharide Derivative 15) (52 g).

The degree of substitution of the resultant hydroxyethylcellulose derivative by polyoxyalkylene-containing substituent groups (A) was 0.0135.

Preparation Example 16

Preparation of Compound 16

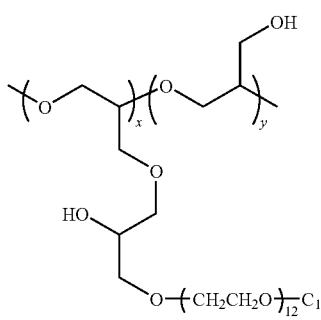

Compound 16

Polyglycidol having a weight average molecular weight of 5,400 (3 g), DMSO (100 g) and granular NaOH (0.16 g) were combined, and then stirred at 70° C. After the solution became homogeneous, the solution was cooled. At room temperature, a compound (0.765 g) represented by the following formula:

was added, followed by aging at 80° C. for 8 hours. Subsequent to cooling, acetic acid (0.23 mL) was added for neutralization. DMSO was distilled off, and the resultant pale yellow, viscous solid was washed with IPA (30 mL×3). After drying under reduced pressure, Compound 16 (2.9 g) was obtained.

The degree of substitution of Compound 16 so obtained by polyoxyalkylene-containing substituent groups (A) was 0.0053.

Preparation Example 17

Preparation of Compound 17

Compound 17

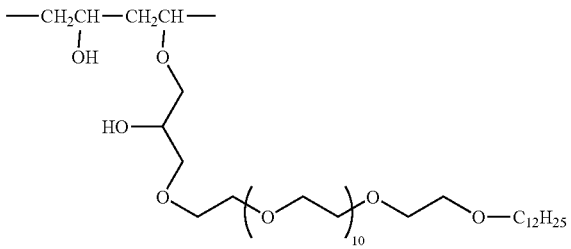

Polyvinyl alcohol having a weight average molecular weight of 2,000 (20 g), DMSO (200 g) and granular NaOH (1.81 g) were combined, and then stirred at 70° C. After the solution became homogeneous, the solution was cooled. At room temperature, a compound (1.87 g) represented by the following formula:

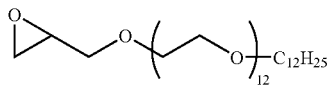

was added, followed by aging at 80° C. for 8 hours. Subsequent to cooling, acetic acid (2.59 mL) was added for neutralization. The reaction product was added into IPA. The precipitated white solid was collected by filtration, and the resultant solid was washed with IPA (300 mL×3). After drying under reduced pressure, Compound 17 (19.0 g) was obtained.

The degree of substitution of Compound 17 so obtained by polyoxyalkylene-containing substituent groups (A) was 0.0033.

Preparation Example 18

Preparation of Compound 18

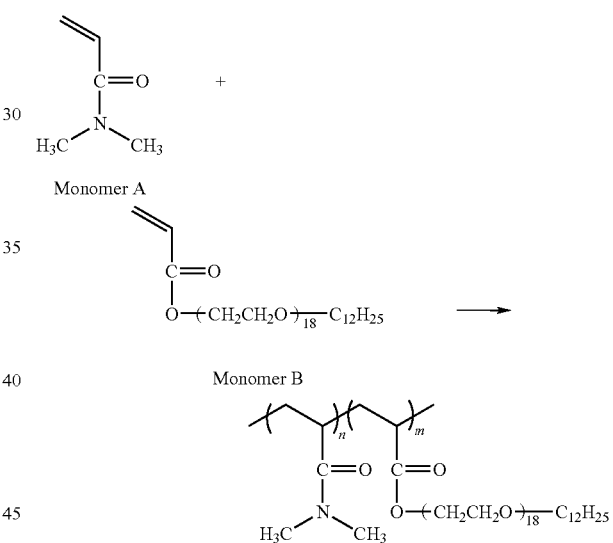

Compound 18

Monomer A (97.1 g), Monomer B (20.7 g) and ethanol (180 g) were mixed. After nitrogen gas was blown into the solution (20 mL/min, 1 hour) to purge air from the interior of the system, the solution was heated to 60° C. Subsequently, a 3 wt. % solution of "V-65" in ethanol (82.8 g) was added dropwise while maintaining the temperature at 60° C. Subsequent to the dropwise addition, aging was conducted at 60° C. for 12 hours. After completion of the reaction, the resulting reaction product was added dropwise into diisopropyl ether (2 kg). The thus-obtained white solid was collected by filtration, and was then washed with diisopropyl ether (500 g× twice). Subsequent to drying under reduced pressure, Compound 18 (105 g) was obtained. The degree of introduction of Monomer B into Compound 18 so obtained was measured by NMR. As a result, it was 0.025. On the other hand, its weight average molecular weight was 51,000.

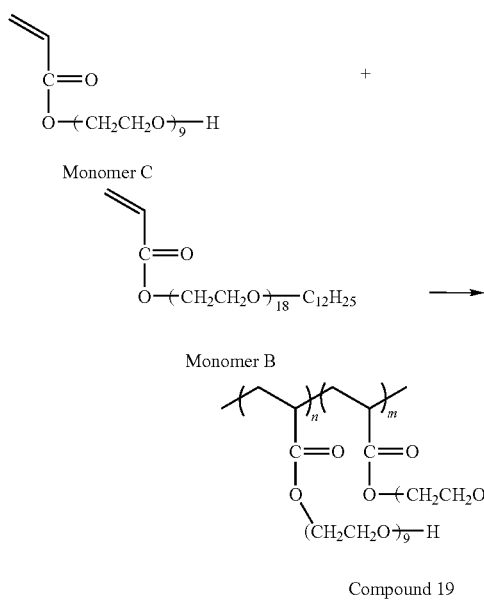

Compound 19

Monomer C (501.8 g), Monomer B (20.7 g) and ethanol (780 g) were mixed. After nitrogen was blown into the solution (40 mL/min, 1 hour) to purge air from the interior of the system, the solution was heated to 60° C. Subsequently, a 3 wt. % solution of "V-65" in ethanol (82.8 g) was added dropwise while maintaining the temperature at 60° C. Subsequent to the dropwise addition, aging was conducted at 60° C. for 12 hours. After completion of the reaction, the resulting reaction and was then washed with diisopropyl ether (500 g× twice). Subsequent to drying under reduced pressure, Compound 19 (490 g) was obtained. The degree of introduction of Monomer B into Compound 19 so obtained was measured by NMR. As a result, it was 0.022. On the other hand, its weight average molecular weight was 110,000.

Examples 1-11

Production of Emulsions

In each Example, the polysaccharide (0.15 g) shown in Table 1 and an 86 wt. % aqueous solution of glycerol (5.40 g) were stirred into a homogeneous solution at a speed of 300 rpm/min in a constant-temperature water bath controlled at 30° C. to provide a composition (1). To the composition (1), the hydrophobic substance (3.5 g) shown in Table 1 was then added dropwise under stirring at the same stirring speed and the same temperature. Subsequent to the dropwise addition, the resulting mixture was kept stirred for not less than 15 minutes at the same stirring speed and the same temperature. Deionized water was added, followed by stirring for 15 minutes or longer to obtain an o/w emulsion.

Each emulsion produced by the above-described procedure had the following composition (wt. %):

| | |
|---|---|
| Polysaccharide derivative | 0.15% |
| 86 wt. % aq. solution of glycerol | 5.97% |
| Hydrophobic substance | 3.87% |
| Water | 90.00% |

Examples 12-14

Production of Emulsions

In each Example, an o/w emulsion was obtained by a similar procedure as in Examples 1-11 except that the amount of the hydrophobic substance was changed as described in Table 2.

Examples 15-18

Production of Emulsions

Following the procedure of Examples 1-11 except that propylene glycol was used in place of 86% glycerol and using the compositions shown in Table 2, o/w emulsions were obtained.

Examples 19-33

Production of Emulsions

In each Example, the polysaccharide (0.25 g) shown in Table 3 and the hydrophobic substance (5.0 g) were stirred at a speed of 300 rpm/min in a constant-temperature water bath controlled at 30° C. to obtain a polysaccharide/hydrophobic substance dispersion. A 20% aqueous solution of dipropylene glycol (5 g) was then added under stirring at the same stirring speed and the same temperature. Subsequent to completion of the addition, the resulting mixture was kept stirred for not less than 30 minutes at the same stirring speed and the same temperature. Deionized water (40 g) was added, followed by stirring for 15 minutes or longer to obtain an o/w emulsion.

Examples 34-48

Production of Emulsions

Following the procedure of Examples 19-33 except that a 30% aqueous solution of dipropylene glycol was used in place of the 20% aqueous solution of dipropylene glycol and using the compositions shown in Table 4, o/w emulsions were obtained.

Examples 49-63

Production of Emulsions

Following the procedure of Examples 19-33 except that a 40% aqueous solution of dipropylene glycol was used in place of the 20% aqueous solution of dipropylene glycol and using the compositions shown in Table 5, o/w emulsions were obtained.

Examples 64-73

Production of Emulsions

Using the compositions shown in Table 6 and following the procedure of Examples 19-33, o/w emulsions were obtained.

Examples 74-77

Production of Emulsions

Using the compositions shown in Table 6 and following the procedure of Examples 1-11, o/w emulsions were obtained.

Example 78

Production of Emulsion

Using the composition shown in Table 6 and following the procedure of Examples 19-33, an o/w emulsion was obtained.

Examples 79-92

Production of Emulsions

Using the compositions shown in Table 7 and following the procedure of Examples 19-33, o/w emulsions were obtained.

Comparative Examples 1-4

Production of Emulsions

In each Comparative Example, an o/w emulsion was obtained by a similar procedure as in Examples 1-11 except that in place of the polysaccharide derivative, polyoxyethylene (60) hydrogenated castor oil or polyoxyethylene (25) octyldodecyl ether was used in the amount shown in Table 3.

Comparative Example 5

Production of Emulsion

An o/w emulsion was obtained by adding the hydrophobic substance shown in Table 8 dropwise to the polysaccharide derivative (0.15 g) shown in Table 8 without using an 86 wt. % aqueous solution of glycerol and conducting treatment under similar conditions as in Examples 1-11.

Comparative Examples 6-7

Production of Emulsions

In each Comparative Example, the corresponding polysaccharide derivative, 86% aqueous solution of glycerol, hydrophobic substance and deionized water, which are shown in Table 8, were mixed to obtain an o/w emulsion.

Test 1

Emulsion Stability Test

The emulsions obtained in the above-describe Examples and Comparative Examples were stored at room temperature and 40° C. for one month, and were visually evaluated for stability (occurrence or non-occurrence of separation).

Further, each emulsion (0.5 g) was diluted with physiological saline (99.5 g), and using the "Model TA-II Coulter Counter", its particle size was measured at room temperature with 50 μm apertures.

The thus-obtained results of stability and average emulsion particle sizes are shown in Tables 1 through 8.

Test 2

Organoleptic Test

The feel of the emulsion obtained in each of the above-described Examples and Comparative Examples to the skin was organoleptically evaluated in accordance with the following 4-level grading scale:

4: Specific feeling to the touch that an emulsion is broken on the skin and the repelled oil is felt.
3: Specific feeling to the touch that an emulsion is broken on the skin and the repelled oil is slightly felt.
2: Specific feeling to the touch that an emulsion is broken on the skin and the repelled oil is not felt much.
1: Specific feeling to the touch that an emulsion is broken on the skin and the repelled oil is not felt at all.

Evaluation was conducted by three expert panelists, and their average-scores were used as evaluation scores. The results are shown in Table 1 to Table 8.

TABLE 1

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| Polyoxyethylene (60) hydrogenated castor oil | — | — | — | — | — | — | — | — | — | — | — |
| Polyoxyethylene (25) octyldodecyl ether | — | — | — | — | — | — | — | — | — | — | — |
| Polysaccharide 6 | 0.15 | 0.15 | 0.15 | 0.15 | 0.15 | 0.15 | 0.15 | — | — | — | — |
| Polysaccharide 7 | — | — | — | — | — | — | — | 0.15 | 0.15 | 0.15 | 0.15 |
| 86% Glycerol | 5.97 | 5.97 | 5.97 | 5.97 | 5.97 | 5.97 | 5.97 | 5.97 | 5.97 | 5.97 | 5.97 |
| Perfluoropolyether, FOMBLIN HC04 | 3.87 | — | — | — | — | — | — | — | — | — | — |
| Silicone oil, KF96A 6Cs | — | 3.87 | — | — | — | — | — | 3.87 | — | — | — |
| Squalane | — | — | 3.87 | — | — | — | 1.00 | — | — | — | — |
| Sunflower oil | — | — | — | 3.87 | — | — | 2.87 | — | 3.87 | — | 2.00 |
| Glycerol myristate isostearate | — | — | — | — | 3.87 | — | — | — | — | — | 1.87 |
| 2-Ethylhexyl paramethoxycinnamate | — | — | — | — | — | 3.87 | — | — | — | 3.87 | — |
| Deionized water | Balance | Balance | Balance | Balance | Balance | Balance | Balance | Balance | Balance | Balance | Balance |
| Emulsified state shortly after preparation | o/w | o/w | o/w | o/w | o/w | o/w | o/w | o/w | o/w | o/w | o/w |
| Average emulsion particle size (μm) | 15 | 16 | 13 | 11 | 11 | 10 | 13 | 15 | 14 | 12 | 14 |
| Stability (room temp., 1 month) | Good | Good | Good | Good | Good | Good | Good | Good | Good | Good | Good |
| Stability (40° C., 1 month) | Good | Good | Good | Good | Good | Good | Good | Good | Good | Good | Good |
| Average score of organoleptic evaluation | 3.7 | 4 | 3.7 | 3.7 | 3.3 | 3 | 3.3 | 3.7 | 3.3 | 3 | 3.7 |

TABLE 2

| | Example | | | | | | |
|---|---|---|---|---|---|---|---|
| | 12 | 13 | 14 | 15 | 16 | 17 | 18 |
| Polyoxyethylene (60) hydrogenated castor oil | — | — | — | — | — | — | — |
| Polyoxyethylene (25) octyldodecyl ether | — | — | — | — | — | — | — |
| Polysaccharide 6 | 0.15 | 0.15 | — | 0.15 | 0.15 | — | — |
| Polysaccharide 7 | — | — | 0.15 | — | — | 0.15 | 0.15 |
| 86% Glycerol | 5.97 | 5.97 | 5.97 | — | — | — | — |
| Propylene glycol | — | — | — | 5.97 | 5.97 | 5.97 | 5.97 |
| Perfluoropolyether, FOMBLIN HC04 | — | — | — | — | — | — | — |
| Silicone oil, KF96A 6Cs | — | — | — | — | — | — | — |
| Squalane | — | — | — | — | — | — | — |
| Sunflower oil | 1.7 | — | — | 3.87 | — | — | 2.00 |
| Glycerol myristate isostearate | — | 6.5 | 6.5 | — | — | — | 1.87 |
| 2-Ethylhexyl paramethoxycinnamate | — | — | — | — | 3.87 | 3.87 | — |
| Deionized water | Balance | Balance | Balance | Balance | Balance | Balance | Balance |
| Emulsified state shortly after preparation | o/w | o/w | o/w | o/w | o/w | o/w | o/w |
| Average emulsion particle size (μm) | 8.5 | 19 | 18 | 14 | 12 | 12 | 13 |
| Stability (room temp., 1 month) | Good | Good | Good | Good | Good | Good | Good |
| Stability (40° C., 1 month) | Good | Good | Good | Good | Good | Good | Good |
| Average score of organoleptic evaluation | 3 | 4.3 | 4.3 | 3.3 | 3.7 | 3 | 3.3 |

TABLE 3

| | Example | | | | | | | | | | | | | | |
|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 |
| Polyoxyethylene (60) Hydrogenated castor oil | — | — | — | — | — | — | — | — | — | — | — | — | — | — | — |
| Polyoxyethylene (25) Octyldodecyl ether | — | — | — | — | — | — | — | — | — | — | — | — | — | — | — |
| Polysaccharide 9 | 0.25 | 0.25 | 0.25 | 0.25 | 0.25 | — | — | — | — | — | — | — | — | — | — |
| Polysaccharide 10 | — | — | — | — | — | 0.25 | 0.25 | 0.25 | 0.25 | 0.25 | — | — | — | — | — |
| Polysaccharide 11 | — | — | — | — | — | — | — | — | — | — | 0.25 | 0.25 | 0.25 | 0.25 | 0.25 |
| 20% Aq. soln. of dipropylene glycol | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 |
| Perfluoropolyether, FOMBLIN HC04 | 5.0 | — | — | — | — | 5.0 | — | — | — | — | 5.0 | — | — | — | — |
| Silicone oil, KF96A 6cs | — | 5.0 | — | — | — | — | 5.0 | — | — | — | — | 5.0 | — | — | — |
| Squalane | — | — | 5.0 | — | — | — | — | 5.0 | — | — | — | — | 5.0 | — | — |
| Sunflower oil | — | — | — | 5.0 | — | — | — | — | 5.0 | — | — | — | — | 5.0 | — |
| 2-Ethylhexyl paramethoxycinnamate | — | — | — | — | 5.0 | — | — | — | — | 5.0 | — | — | — | — | 5.0 |
| Deionized water | 40 | 40 | 40 | 40 | 40 | 40 | 40 | 40 | 40 | 40 | 40 | 40 | 40 | 40 | 40 |
| Emulsified state shortly after preparation | o/w | o/w | o/w | o/w | o/w | o/w | o/w | o/w | o/w | o/w | o/w | o/w | o/w | o/w | o/w |
| Average emulsion particle size (μm) | 14 | 13 | 10 | 11 | 12 | 15 | 14 | 11 | 11 | 13 | 16 | 14 | 11 | 11 | 12 |
| Stability (room temp., 1 month) | Good | Good | Good | Good | Good | Good | Good | Good | Good | Good | Good | Good | Good | Good | Good |
| Stability (40° C., 1 month) | Good | Good | Good | Good | Good | Good | Good | Good | Good | Good | Good | Good | Good | Good | Good |
| Average score of organoleptic evaluation | 3.7 | 4 | 3.7 | 3.7 | 3.3 | 3.7 | 4 | 3.7 | 3.7 | 3 | 3.7 | 4 | 3.7 | 3.3 | 3 |

TABLE 4

| | Example | | | | | | | | | | | | | | |
|---|---|---|---|---|---|---|---|---|---|---|---|---|---|---|---|
| | 34 | 35 | 36 | 37 | 38 | 39 | 40 | 41 | 42 | 43 | 44 | 45 | 46 | 47 | 48 |
| Polyoxyethylene (60) hydrogenated castor oil | — | — | — | — | — | — | — | — | — | — | — | — | — | — | — |
| Polyoxyethylene (25) octyldodecyl ether | — | — | — | — | — | — | — | — | — | — | — | — | — | — | — |
| Polysaccharide 9 | 0.25 | 0.25 | 0.25 | 0.25 | 0.25 | — | — | — | — | — | — | — | — | — | — |
| Polysaccharide 10 | — | — | — | — | — | 0.25 | 0.25 | 0.25 | 0.25 | 0.25 | — | — | — | — | — |

TABLE 4-continued

| | Example | | | | | | | | | | | | | | |
|---|---|---|---|---|---|---|---|---|---|---|---|---|---|---|---|
| | 34 | 35 | 36 | 37 | 38 | 39 | 40 | 41 | 42 | 43 | 44 | 45 | 46 | 47 | 48 |
| Polysaccharide 11 | — | — | — | — | — | — | — | — | — | — | 0.25 | 0.25 | 0.25 | 0.25 | 0.25 |
| 30% Aq. soln. of dipropylene glycol | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 |
| Perfluoropolyether, FOMBLIN HC04 | 5.0 | — | — | — | — | 5.0 | — | — | — | — | 5.0 | — | — | — | — |
| Silicone oil, KF96A 6cs | — | 5.0 | — | — | — | — | 5.0 | — | — | — | — | 5.0 | — | — | — |
| Squalane | — | — | 5.0 | — | — | — | — | 5.0 | — | — | — | — | 5.0 | — | — |
| Sunflower oil | — | — | — | 5.0 | — | — | — | — | 5.0 | — | — | — | — | 5.0 | — |
| 2-Ethylhexyl paramethoxycinnamate | — | — | — | — | 5.0 | — | — | — | — | 5.0 | — | — | — | — | 5.0 |
| Deionized water | 40 | 40 | 40 | 40 | 40 | 40 | 40 | 40 | 40 | 40 | 40 | 40 | 40 | 40 | 40 |
| Emulsified state shortly after preparation | o/w | o/w | o/w | o/w | o/w | o/w | o/w | o/w | o/w | o/w | o/w | o/w | o/w | o/w | o/w |
| Average emulsion particle size (μm) | 13 | 13 | 10 | 10 | 11 | 15 | 15 | 12 | 11 | 13 | 15 | 14 | 12 | 11 | 13 |
| Stability (room temp., 1 month) | Good | Good | Good | Good | Good | Good | Good | Good | Good | Good | Good | Good | Good | Good | Good |
| Stability (40° C., 1 month) | Good | Good | Good | Good | Good | Good | Good | Good | Good | Good | Good | Good | Good | Good | Good |
| Average score of organoleptic evaluation | 3.7 | 4 | 3.7 | 3.7 | 3 | 3.7 | 4 | 4 | 3.7 | 3 | 3.7 | 4 | 4 | 3.7 | 3.3 |

TABLE 5

| | Example | | | | | | | | | | | | | | |
|---|---|---|---|---|---|---|---|---|---|---|---|---|---|---|---|
| | 49 | 50 | 51 | 52 | 53 | 54 | 55 | 56 | 57 | 58 | 59 | 60 | 61 | 62 | 63 |
| Polyoxyethylene (60) hydrogenated castor oil | — | — | — | — | — | — | — | — | — | — | — | — | — | — | — |
| Polyoxyethylene (25) octyldodecyl ether | — | — | — | — | — | — | — | — | — | — | — | — | — | — | — |
| Polysaccharide 9 | 0.25 | 0.25 | 0.25 | 0.25 | 0.25 | — | — | — | — | — | — | — | — | — | — |
| Polysaccharide 10 | — | — | — | — | — | 0.25 | 0.25 | 0.25 | 0.25 | 0.25 | — | — | — | — | — |
| Polysaccharide 11 | — | — | — | — | — | — | — | — | — | — | 0.25 | 0.25 | 0.25 | 0.25 | 0.25 |
| 40% Aq. soln. of dipropylene glycol | 5.0 | 5.0 | 5.0 | 5.0 | 5.0 | 5.0 | 5.0 | 5.0 | 5.0 | 5.0 | 5.0 | 5.0 | 5.0 | 5.0 | 5.0 |
| Perfluoropolyether, FOMBLIN HC04 | 5.0 | — | — | — | — | 5.0 | — | — | — | — | 5.0 | — | — | — | — |
| Silicone oil, KF96A 6cs | — | 5.0 | — | — | — | — | 5.0 | — | — | — | — | 5.0 | — | — | — |
| Squalane | — | — | 5.0 | — | — | — | — | 5.0 | — | — | — | — | 5.0 | — | — |
| Sunflower oil | — | — | — | 5.0 | — | — | — | — | 5.0 | — | — | — | — | 5.0 | — |
| 2-Ethylhexyl paramethoxycinnamate | — | — | — | — | 5.0 | — | — | — | — | 5.0 | — | — | — | — | 5.0 |
| Deionized water | 40 | 40 | 40 | 40 | 40 | 40 | 40 | 40 | 40 | 40 | 40 | 40 | 40 | 40 | 40 |
| Emulsified state shortly after preparation | o/w | o/w | o/w | o/w | o/w | o/w | o/w | o/w | o/w | o/w | o/w | o/w | o/w | o/w | o/w |
| Average emulsion particle size (μm) | 12 | 12 | 9 | 9 | 10 | 15 | 13 | 10 | 9 | 11 | 15 | 13 | 10 | 11 | 12 |
| Stability (room temp., 1 month) | Good | Good | Good | Good | Good | Good | Good | Good | Good | Good | Good | Good | Good | Good | Good |
| Stability (40° C., 1 month) | Good | Good | Good | Good | Good | Good | Good | Good | Good | Good | Good | Good | Good | Good | Good |
| Average score of organoleptic evaluation | 3.3 | 3.7 | 3.3 | 3.3 | 3 | 3.7 | 4 | 3.7 | 3.3 | 3 | 3.7 | 4 | 3.7 | 3.7 | 3.3 |

TABLE 6

| | Example | | | | | | | | | | | | | | |
|---|---|---|---|---|---|---|---|---|---|---|---|---|---|---|---|
| | 64 | 65 | 66 | 67 | 68 | 69 | 70 | 71 | 72 | 73 | 74 | 75 | 76 | 77 | 78 |
| Polyoxyethylene (60) hydrogenated castor oil | — | — | — | — | — | — | — | — | — | — | — | — | — | — | — |
| Polyoxyethylene (25) octyldodecyl ether | — | — | — | — | — | — | — | — | — | — | — | — | — | — | — |
| Polysaccharide 12 | 0.5 | 0.25 | 0.3 | — | — | — | — | — | — | — | — | — | — | — | — |
| Polysaccharide 13 | — | — | — | 0.4 | 0.25 | 0.3 | — | — | — | — | — | — | — | — | — |

TABLE 6-continued

| | Example | | | | | | | | | | | | | | |
|---|---|---|---|---|---|---|---|---|---|---|---|---|---|---|---|
| | 64 | 65 | 66 | 67 | 68 | 69 | 70 | 71 | 72 | 73 | 74 | 75 | 76 | 77 | 78 |
| Polysaccharide 14 | — | — | — | — | — | — | 0.5 | 0.25 | 0.4 | — | — | — | — | — | — |
| Polysaccharide 15 | — | — | — | — | — | — | — | — | — | 0.3 | — | — | — | — | 0.5 |
| Compound 16 | — | — | — | — | — | — | — | — | — | — | 0.3 | — | — | — | — |
| Compound 17 | — | — | — | — | — | — | — | — | — | — | — | 0.3 | — | — | — |
| Compound 18 | — | — | — | — | — | — | — | — | — | — | — | — | 0.3 | — | — |
| Compound 19 | — | — | — | — | — | — | — | — | — | — | — | — | — | 0.3 | — |
| 30% Propylene glycol | 5.0 | 5.0 | 5.0 | 5.0 | 5.0 | 5.0 | 5.0 | 5.0 | 5.0 | 5.0 | — | — | — | — | 5.0 |
| 86% Glycerol | — | — | — | — | — | — | — | — | — | — | 3.0 | 3.0 | 3.0 | 3.0 | — |
| Silicone oil, KF96A 6cs | 5.0 | — | — | 5.0 | — | — | 5.0 | — | — | — | — | — | — | — | — |
| Squalane | — | — | 3.0 | — | — | 4.0 | — | — | 2.5 | 4.0 | — | — | — | — | — |
| Sunflower oil | — | 5.0 | — | — | 5.0 | — | — | 5.0 | — | — | 3.0 | 3.0 | 3.0 | 3.0 | 5.0 |
| 2-Ethylhexyl paramethoxycinnamate | — | — | 2.0 | — | — | 1.0 | — | — | 2.5 | 1.0 | — | — | — | — | — |
| Deionized water | 40 | 40 | 40 | 40 | 40 | 40 | 40 | 40 | 40 | 40 | 40 | 40 | 40 | 40 | 40 |
| Emulsified state shortly after preparation | o/w | o/w | o/w | o/w | o/w | o/w | o/w | o/w | o/w | o/w | o/w | o/w | o/w | o/w | o/w |
| Average emulsion particle size (μm) | 14 | 11 | 14 | 15 | 11 | 15 | 14 | 10 | 13 | 14 | 10 | 9 | 11 | 11 | 13 |
| Stability (room temp., 1 month) | Good | Good | Good | Good | Good | Good | Good | Good | Good | Good | Good | Good | Good | Good | Good |
| Stability (40° C., 1 month) | Good | Good | Good | Good | Good | Good | Good | Good | Good | Good | Good | Good | Good | Good | Good |
| Average score of organoleptic evaluation | 3.5 | 3.0 | 3.7 | 3.5 | 3.0 | 3.7 | 3.5 | 3.1 | 3.4 | 3.7 | 3.2 | 3.0 | 3.1 | 3.1 | 3.3 |

TABLE 7

| | Example | | | | | | | | | | | | | |
|---|---|---|---|---|---|---|---|---|---|---|---|---|---|---|
| | 79 | 80 | 81 | 82 | 83 | 84 | 85 | 86 | 87 | 88 | 89 | 90 | 91 | 92 |
| Polyoxyethylene (60) hydrogenated castor oil | — | — | — | — | — | — | — | — | — | — | — | — | — | — |
| Polyoxyethylene (25) octyldodecyl ether | — | — | — | — | — | — | — | — | — | — | — | — | — | — |
| Polysaccharide 9 | 0.5 | 0.25 | — | — | — | — | — | — | — | — | — | — | — | — |
| Polysaccharide 10 | — | — | 0.5 | 0.25 | — | — | — | — | — | — | — | — | — | — |
| Polysaccharide 11 | — | — | — | — | 0.5 | 0.25 | — | — | — | — | — | — | — | — |
| Polysaccharide 12 | — | — | — | — | — | — | 0.5 | 0.25 | — | — | — | — | — | — |
| Polysaccharide 13 | — | — | — | — | — | — | — | — | 0.5 | 0.25 | — | — | — | — |
| Polysaccharide 14 | — | — | — | — | — | — | — | — | — | — | 0.4 | 0.3 | — | — |
| Polysaccharide 15 | — | — | — | — | — | — | — | — | — | — | — | — | 0.5 | 2.0 |
| 60% 1,3-Butanediol | 10.0 | 5.0 | 10.0 | 5.0 | 10.0 | 5.0 | 10.0 | 5.0 | 10.0 | 5.0 | 10.0 | 5.0 | 10.0 | 5.0 |
| Vaseline | 5.0 | — | 9.0 | — | 7.0 | — | 7.0 | — | 7.0 | — | 5.0 | — | 3.0 | — |
| Sunflower oil | — | 10.0 | — | 7.0 | — | 8.0 | — | 7.5 | — | 7.0 | — | 9.0 | — | 6.0 |
| 2-Ethylhexyl paramethoxycinnamate | 5.0 | — | 1.0 | — | 3.0 | — | 3.0 | — | 3.0 | — | 5.0 | — | 7.0 | — |
| Deionized water | 40 | 40 | 40 | 40 | 40 | 40 | 40 | 40 | 40 | 40 | 40 | 40 | 40 | 40 |
| Emulsified state shortly after preparation | o/w | o/w | o/w | o/w | o/w | o/w | o/w | o/w | o/w | o/w | o/w | o/w | o/w | o/w |
| Average emulsion particle size (μm) | 16 | 13 | 15 | 13 | 14 | 12 | 15 | 12 | 14 | 12 | 12 | 11 | 13 | 14 |
| Stability (room temp., 1 month) | Good | Good | Good | Good | Good | Good | Good | Good | Good | Good | Good | Good | Good | Good |
| Stability (40° C., 1 month) | Good | Good | Good | Good | Good | Good | Good | Good | Good | Good | Good | Good | Good | Good |
| Average score of organoleptic evaluation | 3.8 | 3.7 | 3.8 | 3.7 | 3.7 | 3.3 | 3.7 | 3.2 | 3.5 | 3.1 | 3.2 | 3.2 | 3.2 | 3.5 |

TABLE 8

| | Comparative Example | | | | | | |
|---|---|---|---|---|---|---|---|
| | 1 | 2 | 3 | 4 | 5 | 6 | 7 |
| Polyoxyethylene (60) hydrogenated castor oil | 0.20 | 0.20 | 1.50 | — | — | — | — |
| Polyoxyethylene (25) octyldodecyl ether | — | — | — | 1.50 | — | — | — |

TABLE 8-continued

|  | Comparative Example | | | | | | |
|---|---|---|---|---|---|---|---|
|  | 1 | 2 | 3 | 4 | 5 | 6 | 7 |
| Polysaccharide 6 | — | — | — | — | 0.15 | 0.5 | — |
| Polysaccharide 7 | — | — | — | — | — | — | 0.5 |
| 86% Glycerol | 5.97 | 5.97 | 5.97 | 5.97 | — | 9.5 | 9.5 |
| Perfluoropolyether, FOMBLIN HC04 | 3.87 | — | — | — | — | — | — |
| Silicone oil, KF96A 6Cs | — | — | — | — | — | — | — |
| Squalane | — | 3.87 | 3.87 | 3.87 | 3.87 | — | 5 |
| Sunflower oil | — | — | — | — | — | 5 | — |
| Glycerol myristate isostearate | — | — | — | — | — | — | — |
| 2-Ethylhexyl paramethoxycinnamate | — | — | — | — | — | — | — |
| Deionized water | Balance | Balance | Balance | Balance | Balance | Balance | Balance |
| Emulsified state shortly after preparation | Separated | o/w | o/w | o/w | Separated | o/w | o/w |
| Average emulsion particle size (μm) | — | 14 | 1 | 10 | — | — | — |
| Stability (room temp., 1 month) | — | Separated | Good | Separated | — | Separated | Separated |
| Stability (40° C., 1 month) | — | Separated | Good | Separated | — | Separated | Separated |
| Average score of organoleptic evaluation | — | — | 1.7 | — | — | — | — |

INDUSTRIAL APPLICABILITY

Emulsions obtained in accordance with the process of the present invention are excellent in touch feeling to the skin and good in stability. The emulsions of the present invention are, therefore, useful for products such as cosmetics, massaging cosmetic preparations and skin care preparations.

The invention claimed is:

1. A process for the preparation of an o/w emulsion, which comprises:
    mixing together a high molecular weight compound, an aqueous solution of a water-soluble polyol, and a hydrophobic compound, and diluting the resulting mixture with water;
    wherein said high molecular weight compound carrying at least on side chains thereof is a group represented by the following formula (1):

—(OX)$_n$-E$^2$-R    (1)

wherein said high molecular weight compound is a synthetic, water-soluble, compound having a molecular weight of from 10,000 to 2,000,000, wherein OX of formula (1) is an ethylene oxide (EO) group, E$^2$ represents an ether bond or an oxycarbonyl group (—OCO— or —COO—), n is a number of 5 to 200, and R is a linear or branched C$_{4-30}$ hydrophobic group having 5 to 200 EO linkages added at a rate of from 0.0001 to 0.1 group per backbone monomer,
    wherein said high molecular weight compound being obtained by:
        (i) copolymerizing a water-soluble monomer of the following formula (5) or formula (6) with a water-soluble monomer having a C$_{4-30}$ hydrophobic group bonded via 5 to 200 EO linkages as defined by the following formula (7):

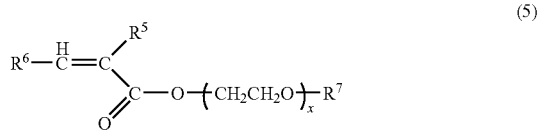

(5)

wherein R$^5$, R$^6$ and R$^7$ are the same or different and each independently represents a hydrogen atom or a methyl group, and X stands for a number of from 2 to 100,

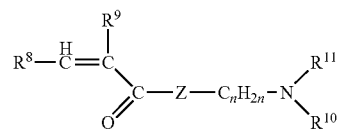

(6)

wherein R$^8$ and R$^9$ are the same or different and each independently represents a hydrogen atom or a methyl group, R$^{10}$ and R$^{11}$ each independently represents a methyl group or an ethyl group, n stands for an integer of 0 or 2 to 5, and Z represents an NH group, an oxygen atom, or connecting bond, and

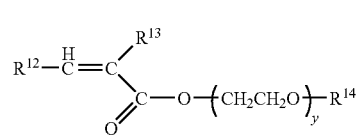

(7)

wherein R$^{12}$ and R$^{13}$ are the same or different and each independently represents a hydrogen atom or a methyl group, y stands for a number of 5 to 200, and R$^{14}$ represents a linear or branched C$_{8-30}$ alkyl group optionally substituted by hydroxyl group(s).

2. The process according to claim 1 for the preparation of an o/w emulsion, wherein:
    (a) 1 part by weight of said high molecular weight compound,
    (b) 2 to 50 parts by weight of one or more aqueous solutions of water-soluble polyols,
    (c) 5 to 30 parts by weight of water, and
    (d) 0.01 to 70 parts by weight of said hydrophobic compound are mixed to obtain a composition (1), and said composition is then diluted wit water.

3. The process according to claim 2 for the preparation of an o/w emulsion, wherein a weight ratio of said water-soluble polyols to said water in said composition (1) is from 10/90 to 99/1.

4. The process according to claim 2 for the preparation of an o/w emulsion, wherein said water-soluble polyols and water or said aqueous solutions of said water-soluble polyols are added to and mixed with a mixture of said high molecular weight compound and said hydrophobic compound to obtain said composition (1), and said composition (1) is then diluted with water.

5. The process according to claim 2 for the preparation of an o/w emulsion, wherein subsequent to mixing of said high molecular weight compound, said water-soluble polyols and water or mixing of said high molecular weight compound and said aqueous solutions of said water-soluble polyols, said hydrophobic compound is added and mixed to obtain said composition (1), and said composition (1) is then diluted with water.

* * * * *